United States Patent
Miwa et al.

(10) Patent No.: US 9,528,961 B2
(45) Date of Patent: Dec. 27, 2016

(54) EXHAUST GAS SENSOR

(71) Applicants: Tomohiro Miwa, Toyota (JP); Sumio Kamiya, Toyota (JP); Hirotaka Sakakibara, Toyota (JP); Tomoaki Shinma, Toyota (JP)

(72) Inventors: Tomohiro Miwa, Toyota (JP); Sumio Kamiya, Toyota (JP); Hirotaka Sakakibara, Toyota (JP); Tomoaki Shinma, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 256 days.

(21) Appl. No.: 14/405,567

(22) PCT Filed: Jul. 24, 2013

(86) PCT No.: PCT/IB2013/001600
§ 371 (c)(1),
(2) Date: Dec. 4, 2014

(87) PCT Pub. No.: WO2014/024017
PCT Pub. Date: Feb. 13, 2014

(65) Prior Publication Data
US 2015/0144487 A1 May 28, 2015

(30) Foreign Application Priority Data

Aug. 7, 2012 (JP) ................. 2012-175334

(51) Int. Cl.
*G01N 27/407* (2006.01)
*G01N 27/409* (2006.01)

(52) U.S. Cl.
CPC ........ *G01N 27/409* (2013.01); *G01N 27/4072* (2013.01); *G01N 27/4075* (2013.01); *G01N 27/4077* (2013.01)

(58) Field of Classification Search
CPC .... G01N 27/409; G01N 27/41; G01N 27/407; G01N 27/4075; F01N 2560/00–2560/028; F01N 2570/007
See application file for complete search history.

(56) References Cited

U.S. PATENT DOCUMENTS 5,271,821 A    12/1993  Ogasawara et al.
2011/0220496 A1*  9/2011  Oya ..................... G01N 27/407
                                                  204/424

FOREIGN PATENT DOCUMENTS

JP    02-276956 A    11/1990
JP    2007-163272 A    6/2007
(Continued)

*Primary Examiner* — Alexander Noguerola
(74) *Attorney, Agent, or Firm* — Sughrue Mion, PLLC (57) ABSTRACT

An exhaust gas sensor (100; 200) is configured so as to detect an oxygen concentration or air-fuel ratio in exhaust gas. The exhaust gas sensor includes a sensor element (10) and a manganese reaction layer (20). The sensor element detects an oxygen concentration or air-fuel ratio. The manganese reaction layer is formed on at least part of a surface of the sensor element and is formed of a substance containing an element capable of generating a complex oxide having manganese through reaction with a manganese oxide in the exhaust gas. The exhaust gas sensor is configured to detect an oxygen concentration or air-fuel ratio in exhaust gas of an internal combustion engine that utilizes a fuel having a Mn concentration in excess of 20 ppm.

8 Claims, 9 Drawing Sheets

(56) References Cited

FOREIGN PATENT DOCUMENTS

| | | |
|---|---|---|
| JP | 2010-038600 A | 2/2010 |
| JP | 2011-209280 A | 10/2011 |
| JP | 2011-252894 A | 12/2011 |
| JP | 2014-035222 A | 2/2014 |
| WO | 2014/024018 A1 | 2/2014 |

* cited by examiner

RELATED ART

EXHAUST GAS SENSOR

BACKGROUND OF THE INVENTION

1. Field of the Invention

The invention relates to an exhaust gas sensor.

2. Description of Related Art

Gas sensors that utilize sensor elements have been used conventionally in order to detect specific gases in the atmosphere. Such gas sensors, for instance, can detect the concentration of a specific gas component such as hydrocarbons (HC), oxygen ($O_2$) or the like that are present in the exhaust gas of automobiles. To that end, one such gas sensor is provided in the exhaust passage of an internal combustion engine, for instance an automobile engine. The gas sensor is used to control an exhaust gas control apparatus. Conventional oxygen sensor elements that detect the concentration of oxygen in exhaust gas include, for instance, oxygen concentration-electromotive force sensors that have a $ZrO_2$ solid electrolyte.

Figure 15:
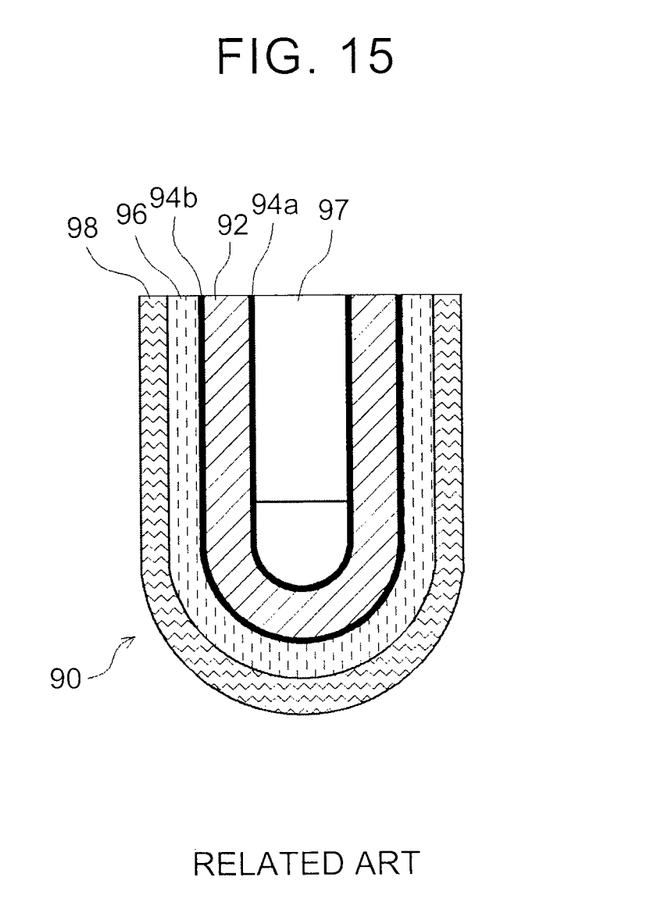
FIG. 15 is a diagram illustrating schematically a gas sensor in the related art.

As illustrated in FIG. 15, an oxygen sensor element 90, in the form of a bottomed cylinder, is configured through sequential layering of an inner electrode 94a, a solid electrolyte layer 92, an outer electrode 94b, and a diffusion resistance layer 96. A heater 97 is inserted inward of the inner electrode 94a. Exhaust gas reaches the outer electrode 94b through micro-holes in the diffusion resistance layer 96, and a sensor output is obtained between the outer electrode 94b and the inner electrode 94a. The diffusion resistance layer 96 is formed of a porous ceramic coating, with a view to imparting a function of limiting the flow rate of exhaust gas that reaches the outer electrode 94b and of protecting the outer electrode 94b.

The exhaust gas contains noxious substances that include components present in oil, for instance P, Ca or Zn, as well as gasoline additive components such as K or Na. Therefore, in cases where such a sensor element is used in an exhaust gas sensor for automobiles, a problem may arise in that the sensor element may become contaminated by these noxious substances. To address this problem, it has been proposed to cover the periphery of the sensor element with a porous protective layer (trap layer) 98 (FIG. 15). In the above technology, noxious substances in the exhaust gas become adsorbed onto the protective layer 98. As a result, this allows suppressing intrusion of the noxious substances into the sensor element. Japanese Patent Application Publication No. 2011-252894 (JP 2011-252894 A) is an instance of related art pertaining to such gas sensors.

SUMMARY OF THE INVENTION

Improving thermal efficiency by increasing the compression ratio of the engine is an effective way of improving fuel economy in an automobile. However, knocking occurs readily in engines of high compression ratio, and hence the engine requires a high-octane fuel. Studies in recent years have addressed the addition of Mn-containing additives to fuel in order to increase the octane number of fuel.

The inventors focused on the phenomenon of delayed (worsened) sensor response in internal combustion engines that utilize a fuel containing the abovementioned Mn component. The inventors analyzed in detail the influence that the Mn component in the fuel exerts on sensor response, and arrived at the findings below.

When becoming adhered to the sensor element, the Mn component in fuel is deposited in the form of a Mn oxide. When, in that state, exhaust gas having a high oxygen concentration flows into the gas sensor, the Mn oxide adhered on the sensor element becomes oxidized, and oxygen in the exhaust gas is consumed as the oxidation reaction $Mn_3O_4+O_2 \rightarrow Mn_2O_3$ progresses. As a result, the oxygen concentration in the exhaust gas that reaches the sensor electrode becomes lower than the actual one. The abovementioned oxidation reaction continues, in that state, until completion. Accordingly, the sensor value takes on a value that is lower than the actual oxygen concentration until the abovementioned oxidation reaction is over. Thus, the response in a case where exhaust gas of high oxygen concentration flows into the gas sensor becomes delayed.

On the other hand, when exhaust gas of low oxygen concentration flows into the gas sensor, the Mn oxide adhered to the sensor element becomes reduced, and oxygen is released into the exhaust gas as the opposite reaction proceeds, i.e. the reduction reaction $Mn_2O_3 \rightarrow Mn_3O_4+O_2$. As a result, the oxygen concentration in the exhaust gas that reaches the sensor electrode is higher than the actual one. The state where the oxygen concentration is higher than the actual one continues until completion of the abovementioned reduction reaction. Accordingly, the sensor value takes on a value that is higher than the actual oxygen concentration, until the abovementioned reduction reaction is over. The response in a case where exhaust gas of low oxygen concentration flows into the gas sensor becomes thus delayed. In this way, the response of the sensor becomes delayed through the occurrence of oxygen absorption and release (oxygen storage capacity, OSC) reaction that accompanies changes in the valence of Mn. A mechanism for effectively preventing the abovementioned OSC is accordingly required.

The invention provides an exhaust gas sensor that is based on the above findings.

The exhaust gas sensor, being an aspect of the invention, is configured so as to detect an oxygen concentration or air-fuel ratio in exhaust gas. The exhaust gas sensor includes a sensor element and a manganese reaction layer. The sensor element detects an oxygen concentration or air-fuel ratio. The manganese reaction layer is formed on at least part of a surface of the sensor element and is formed of a substance containing an element capable of generating a complex oxide having manganese through reaction with a manganese oxide in the exhaust gas. Furthermore, the exhaust gas sensor is configured to detect an oxygen concentration or air-fuel ratio in exhaust gas of an internal combustion engine that utilizes a fuel having a Mn concentration in excess of 20 ppm.

In the exhaust gas sensor thus configured, the manganese reaction layer is formed on at least part of a surface of the sensor element. The manganese reaction layer is made up of a substance that contains an element capable of generating a complex oxide having manganese through reaction with a manganese oxide (for instance, $Mn_3O_4$) in exhaust gas. Therefore, the manganese oxide in the exhaust gas is replaced by a complex oxide that has manganese, through reaction with the manganese reaction layer. Such a complex oxide is superior to the manganese oxide in thermal and chemical stability in oxidizing and reducing atmospheres. This results in a lower likelihood of occurrence of the oxidation reaction $Mn_3O_4+O_2 \rightarrow Mn_2O_3$ or the reduction reaction $Mn_2O_3 \rightarrow Mn_3O_4+O_2$, such as those that occur when a manganese oxide remains adhered on the surface of the sensor element. As a result, changes in oxygen concentration in the exhaust gas around the sensor element are curtailed, and the sensor response delay can be reduced.

In the aspect of the invention, the manganese reaction layer may contain at least one element from among Zn, B, Ca, Ba, Sr, V and Y, as the element capable of generating a complex oxide having manganese.

In the aspect of the invention, at least part of the manganese reaction layer may contains amorphous glass. A glass matrix may make up the amorphous glass includes Si, B, Al, R and M as main constituents. The mass ratios of main components, in terms of oxide, with the entirety of the glass matrix as 100 mass %, may be: $SiO_2$ 25 mass % to 40 mass %; $B_2O_3$ 20 mass % to 35 mass %; $Al_2O_3$ 1 mass % to 10 mass %; $R_2O$ 5 mass % to 20 mass %; M oxide 0 mass % to 25 mass %, and the total of the main components may be 80 mass % or more. R is at least one element from among Li, Na and K. M is at least one element from among Zn, Ca, Ba, Sr, V and Y. The amorphous glass having the abovementioned element generates a complex oxide having manganese through reaction with a manganese oxide in the exhaust gas.

In the aspect of the invention, the glass matrix may include Si, B, Al, K and Zn as main constituents. The mass ratios of main components, in terms of oxide, with the entirety of the glass matrix as 100 mass %, may be: $SiO_2$ 25 mass % to 40 mass %; $B_2O_3$ 20 mass % to 35 mass %; $Al_2O_3$ 1 mass % to 10 mass %; $K_2O$ 5 mass % to 20 mass %; ZnO 15 mass % to 25 mass %, and the total of the main components may be 80 mass % or more. A glass matrix having mainly Zn generates a stable spinel-structure complex oxide (for instance, $ZnMn_2O_4$), through reaction with a manganese oxide. The effect of curtailing delay in the change of oxygen concentration can be efficiently elicited thereby.

In the aspect of the invention, the manganese reaction layer may be formed of oxide particles supported on the surface of the sensor element. The oxide particles may contain at least one element from among Zn, B, Ca, Ba, Sr, V and Y, as the element capable of generating a complex oxide having manganese. The manganese reaction layer made up of the oxide particles that have the above element generates a complex oxide having manganese through reaction with a manganese oxide in the exhaust gas.

In the aspect of the invention, the sensor element may include a stack of a solid electrolyte layer, a heater layer and a porous diffusion resistance layer. A pair of electrodes is provided on either respective side of the solid electrolyte layer. The heater layer includes a heating element that generates heat through energization. The diffusion resistance layer is configured so as to let the exhaust gas through in such a manner that the exhaust gas is introduced to either of the pair of electrodes. The manganese reaction layer is formed of a dense body that does not let the exhaust gas through, and is formed at a region that excludes the diffusion resistance layer. By virtue of the above configuration, a manganese oxide in the exhaust gas can be converted to a complex oxide (typically, a spinel-structure or perovskite-structure complex oxide) having manganese, while the gas permeability of the diffusion resistance layer is secured.

In the aspect of the invention, the sensor element may include a stack of a solid electrolyte layer, a heater layer and a porous diffusion resistance layer. The pair of electrodes is provided on either respective side of the solid electrolyte layer. The heater layer includes a heating element that generates heat through energization. The diffusion resistance layer is configured so as to let the exhaust gas through in such a manner that the exhaust gas is introduced to either of the pair of electrodes. Furthermore, a porous protective layer may be formed so as to cover the diffusion resistance layer. The manganese reaction layer is formed by adding the substance containing an element capable of generating a complex oxide to the porous protective layer. In the above configuration, the porous protective layer also serves as the manganese reaction layer. The configuration of the exhaust gas sensor can be simplified accordingly, in that the manganese reaction layer need not be provided separately.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Embodiments of the invention are explained next. Any features other than the features specifically set forth in the description and which may be necessary for carrying out the invention can be regarded as instances of design matter for a person skilled in the art on the basis of related arts in the technical field in question. The invention may be carried out thus on the basis of the features disclosed in the description and on the basis of common technical knowledge in the technical field in question.

Figure 1:
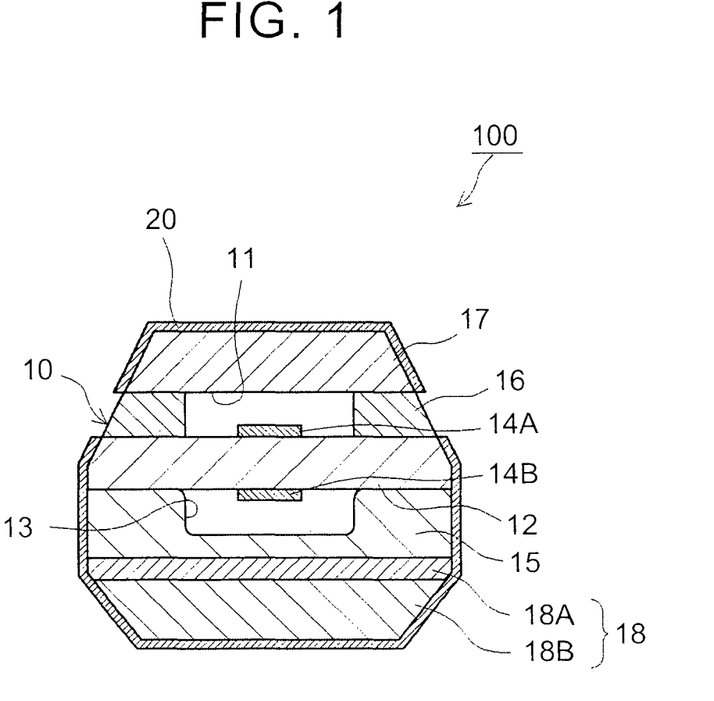
FIG. 1 is a cross-sectional diagram illustrating schematically an exhaust gas sensor according to a first embodiment of the invention.

A gas sensor, as a first embodiment, is an exhaust gas sensor capable of detecting an oxygen concentration or air-fuel ratio in exhaust gas. The exhaust gas sensor is used in order to detect the oxygen concentration or air-fuel ratio in the exhaust gas of an internal combustion engine that utilizes a fuel (typically, gasoline) the Mn concentration whereof exceeds 20 ppm. The structure of an exhaust gas sensor 100 will be explained with reference to FIG. 1. FIG. 1 is a schematic diagram illustrating, in a cross-section, an example of the configuration of a main portion of the exhaust gas sensor 100 of the first embodiment.

As illustrated in FIG. 1, the exhaust gas sensor 100 is provided with a sensor element 10 that detects an oxygen concentration or air-fuel ratio, and with a manganese reaction layer 20 that is formed on at least part of the surface of the sensor element 10.

The sensor element 10 is configured through layering of a solid electrolyte layer 12, a heater layer 18, and a porous diffusion resistance layer 16. A pair of electrodes 14A, 14B is provided on either respective side of the solid electrolyte layer 12. The heater layer 18 has a heating resistor 18A that generates heat when energized. The diffusion resistance layer 16 is configured so as to allow exhaust gas to pass.

The solid electrolyte layer 12 is made up of a solid electrolyte having oxygen ion conductivity. Examples of such a solid electrolyte include, for instance, zirconia (for example, yttria-stabilized zirconia (YSZ)).

The measurement electrode 14A is formed outward of the solid electrolyte layer 12. A measurement gas space 11, into which exhaust gas can be introduced, and having, as one wall, the solid electrolyte layer 12, is formed further outward than measurement electrode 14A. The measurement gas space 11 is defined by the solid electrolyte layer 12, the diffusion resistance layer 16 and the shielding layer 17. The shielding layer 17 has a gas-impervious internal structure, and is made up of alumina in the first embodiment. The diffusion resistance layer 16 is provided at positions that define the measurement gas space 11 around the measurement electrode 14A (herein, at both ends of the measurement gas space 11 in the width direction), in order to restrict the introduction amount of exhaust gas into the measurement electrode 14A. The diffusion resistance layer 16 is a porous body through which exhaust gas is introduced into the measurement gas space 11. Materials that can make up a porous body, for instance, alumina, zirconia, ceria or the like may be used as the material of the diffusion resistance layer 16.

The reference electrode 14B is formed inward of the solid electrolyte layer 12. A reference gas space 13, into which a reference gas such as the atmosphere or the like can be introduced, is formed so as to surround the reference electrode 14B. The reference gas space 13 is defined by the solid electrolyte layer 12 and a protective layer 15. The protective layer 15 has a gas-impervious internal structure, and is herein made up of alumina. The reference electrode 14B and the measurement electrode 14A are both made up of a precious metal having high catalytic activity, for instance platinum or the like.

The heater layer 18 is made up of an insulating base 18B having alumina as a main constituent, and the heating resistor 18A that is stacked on the insulating base 18B. The solid electrolyte layer 12 made up of zirconia or the like has an insulation at normal temperature, but in high-temperature environments the solid electrolyte layer 12 becomes activated and exhibits high oxygen ion conductivity. The heater layer 18 serves as a heating region of the solid electrolyte layer 12. Heating by the heater layer 18 is controlled in such a manner that the activation temperature is reached in the heating region. In the embodiment, the heater layer 18 is disposed outward of the protective layer 15, on the reference electrode 14B side of the solid electrolyte layer 12. The heating resistor 18A is made up of a resistor, for instance of platinum or the like.

The manganese reaction layer 20 is formed on at least part of the surface of the sensor element 10 that is made up of the solid electrolyte layer 12, the diffusion resistance layer 16 and the heater layer 18 described above. In the embodiment, the manganese reaction layer 20 is made up of a dense body that does not let exhaust gas through. The manganese reaction layer 20 is formed on all regions of the surface of the sensor element 10, excluding the porous diffusion resistance layer 16. The manganese reaction layer 20 is made up of a substance that contains an element capable of generating a complex oxide (typically, a spinel-structure or perovskite-structure complex oxide, or a complex oxide having some other crystal structure) having manganese, through a reaction with a manganese oxide (for instance, $Mn_3O_4$) in the exhaust gas. The manganese reaction layer 20 is provided in order to convert a manganese oxide in the exhaust gas into a complex oxide having manganese. That is, a manganese oxide in exhaust gas is replaced, as a result of a reaction with the manganese reaction layer 20, by a stable complex oxide that does not readily undergo valence changes.

The element in the manganese reaction layer 20 is not particularly limited, so long as it is an element (typically, a metal or metalloid element) capable of generating a complex oxide having manganese through reaction with a manganese oxide in the exhaust gas. Preferably, there is used for instance at least one element selected from among zinc (Zn), boron (B), calcium (Ca), barium (Ba), strontium (Sr), vanadium (V) and yttrium (Y), particularly preferably Zn. There may be used one, two or more elements selected from the above element group.

In the embodiment, at least part of the manganese reaction layer 20 has amorphous glass. A glass matrix that makes up the amorphous glass has one, two or more elements from among Zn, B, Ca, Ba, Sr, V and Y, as elements capable of generating a complex oxide having manganese (typically, a spinel-structure or perovskite-structure complex oxide having manganese). Preferred among the foregoing is Zn or B, or a combination of Zn and B. A suitable glass matrix has a composition having a high content of these elements. In a particularly suitable instance, the above element is Zn, or the content of Zn is high (for instance, the content of Zn, in terms of oxide, is 15 mass % or greater). A glass matrix having mainly Zn is preferred in terms of generating a stable complex oxide (for instance, $ZnMn_2O_4$) having manganese as a result of a reaction with a manganese oxide.

Besides the above reaction components, the glass matrix may contain various oxide components ($SiO_2$, $Al_2O_3$, $R_2O$), depending on the intended purpose. Preferably, the amorphous glass that is used in the first embodiment has a component that can promote reactions with a manganese oxide in the exhaust gas. Herein, R denotes one, two or more alkali metal elements from among Li, Na and K. Preferably, there is used amorphous glass of stable composition that does not melt readily in the high-temperature region at which the exhaust gas sensor is used (500° C. to 600° C. in the case of an oxygen sensor, 700° C. to 800° C. in the case of an air-fuel ratio sensor). Preferably, the amorphous glass has a component that allows adjusting the viscosity of the glaze slurry for forming the manganese reaction layer in such a manner that the slurry can be readily applied onto the surface of a sensor element. Any amorphous glass that satisfies such conditions may be used, without particular limitations. Specific examples of elements that can form such amorphous glass include, for instance, Si, B, Al, R and M. As indicated above, R denotes one, two or more alkali metal elements from among Li, Na and K. Preferred among the foregoing is Li or K, or a combination of Li and K. Further, M denotes one, two or more elements from among Zn, Ca, Ba, Sr, V and Y.

Preferably, for instance, $SiO_2$ is 25 mass % to 40 mass %, $B_2O_3$ is 20 mass % to 35 mass %, $Al_2O_3$ is 1 mass % to 10 mass %, $R_2O$ is 5 mass % to 20 mass %, and an M oxide is 0 mass % to 25 mass % in the mass composition of the glass matrix as a whole; and the total of the foregoing main components is 80 mass % or more. More preferably, the total of the above main components is 90 mass % or more in the entire glass. Herein, a Zn component can be calculated as ZnO, a Ca component as CaO, a Ba component as BaO, a Sr component as SrO, a V component as $V_2O_4$, and a Y component as $Y_2O_3$. The reaction with manganese oxide is promoted in the amorphous glass having the foregoing oxide components at the abovementioned mass compositions. Furthermore, the amorphous glass is stable in the high-temperature region at which the exhaust gas sensor is used. Accordingly, the amorphous glass having the oxide components at the abovementioned mass compositions can be appropriately used as amorphous glass that is suitable for the embodiments of the invention.

Preferably, such amorphous glass further contains one, two or more from among NiO, CoO and $MoO_2$. Herein, NiO, CoO and $MoO_2$ are optionally added components. Incorporating these components results in a glass matrix made up of a multi-component system. The chemical and physical characteristics of the glass matrix can be enhanced as a result. The content of these oxides with respect to the whole glass composition is preferably zero (no addition), or 10 mass % or less. Preferably, for instance, the total amount of NiO, CoO and $MoO_2$ is 5 mass % or less (for instance, 0.5 mass % to 5 mass %) of the glass composition as a whole.

Besides the above-described components, other components (for instance, MgO, $La_2O_3$, $ZrO_2$, $SnO_2$, $HfO_2$) that are not essential for carrying out the invention may be added in accordance with the intended use. These components as well contribute to diversifying the glass constitution.

In the technology disclosed herein, the term "amorphous glass" includes conceptually also forms (typically, partially crystallized glass) in which part of the amorphous glass is present as a crystalline phase. A preferred form of the technology disclosed herein is, for instance, amorphous glass that includes mainly an amorphous phase of the above oxide components, and a crystalline phase of ZnO. Reactivity with a manganese oxide can be further enhanced through the presence of such a crystalline phase. The crystalline phase may be mixed into (dispersed in) the amorphous phase, or may be unevenly distributed or precipitated in the vicinity of the surface of the manganese reaction layer.

The manganese reaction layer 20 may be formed as described below. Firstly, compounds for obtaining the various oxide components that make up the glass component (glass matrix) of the manganese reaction layer 20 and, as the case may require, other additives are prepared in the form of glass raw materials (glaze) powders. Typically, the mixture resulting from mixing compounds and additives may be prepared in the form of glass raw materials (glaze) powders. For instance, the above mentioned compounds are industrial products or reagents, or various mineral materials that include oxides, hydroxides, carbonates, sulfates, nitrates, complex oxides or the like containing various components. These glass raw material powders are blended and mixed so as to obtain a desired composition, and thereafter a glaze slurry is prepared wherein the resulting mixture is dispersed in an appropriate solvent (for instance, water). The glaze slurry is applied onto the surface of the sensor element 10, and is fired (baked), to form thereby the manganese reaction layer 20. The glaze slurry may contain an appropriate amount of a clay mineral or organic binder, with a view to, for instance, improving the shape retention of the coating.

Conventional ordinary coating means may be used, without any limitations, in the operation of applying the glaze slurry onto the surface of the sensor element 10. For instance, the glaze slurry may be applied through coating of a predetermined amount of the glaze slurry onto sites, of the sensor element 10, that exclude the diffusion resistance layer 16, using an appropriate coating apparatus (spray atomizer, roller or the like). Thereafter, the manganese reaction layer 20 may be formed on the surface of the sensor element 10 through firing (baking) of the coating, using appropriate firing means. The firing temperature ranges from about 900° C. to about 1,000° C., preferably from about 920° C. to about 980° C. The time over which the firing temperature (highest firing temperature) is held depends on the firing temperature, but ranges from about 0.5 hours to about 2 hours, preferably from about 1 hour to about 1.5 hours. The abovementioned firing may be performed in an air atmosphere.

In the exhaust gas sensor 100 thus configured, the manganese reaction layer 20 made up of amorphous glass is formed in at least part of the surface of the sensor element 10. The amorphous glass contains an element that can generate a complex oxide having manganese (typically, a spinel-structure or perovskite-structure complex oxide having manganese), through reaction with a manganese oxide in the exhaust gas. Therefore, the manganese oxide in the exhaust gas reacts with the manganese reaction layer 20, and is replaced by a stable complex oxide having manganese that does not readily undergo valence changes. This results in a lower likelihood of occurrence of the oxidation reaction $Mn_3O_4+O_2 \rightarrow Mn_2O_3$ or the reduction reaction $Mn_2O_3 \rightarrow Mn_3O_4+O_2$, such as those that occur when a manganese oxide remains adhered on the surface of the sensor element 10. As a result, changes in oxygen concentration in the exhaust gas around the sensor element 10 are curtailed, and the sensor response delay can be reduced.

In the above embodiment, the sensor element 10 is configured in the form of a stack of the solid electrolyte layer 12, the heater layer 18 and the porous diffusion resistance layer 16. The measurement electrode 14A and the reference electrode 14B are respectively provided on either side of the solid electrolyte layer 12. The heater layer 18 has the heating resistor 18A that generates heat when energized. Exhaust gas goes through the diffusion resistance layer 16 to be introduced into the measurement electrode 14A. The manganese reaction layer 20 is made up of a dense body that does not let the exhaust gas through, and is formed at a region that excludes the diffusion resistance layer 16. As a result, a manganese oxide in the exhaust gas can be converted into a complex oxide that has manganese, while the gas permeability of the diffusion resistance layer 16 is secured.

In the above-described embodiment, the manganese reaction layer 20 is made up of amorphous glass, but the substance that contains an element that can generate a complex oxide having manganese is not limited to amorphous glass. For instance, the manganese reaction layer 20 may be formed of crystalline oxide particles that are supported on the surface of the sensor element 10. The crystalline oxide particles exhibit a specific diffraction pattern in an X-ray diffraction spectrum. Such oxide particles may contain one, two or more elements from among Zn, B, Ca, Ba, Sr, V and Y, as the element capable of generating a complex oxide having manganese. Examples of oxides that contain Zn include, for instance, ZnO, and examples of oxides that contain Ca include, for instance, CaO. Examples of oxides that contain Ba include, for instance, BaO, and examples of oxides that contain Sr include, for instance, SrO. Examples of oxides that contain V include, for instance, $V_2O_4$ or the like. Examples of oxides that contain Y include, for instance, $Y_2O_3$ or the like. Examples of oxides that contain B include, for instance, $B_2O_3$ or the like. These oxides generate a complex oxide having manganese as a result of a reaction with a manganese oxide. Such a complex oxide exhibits superior thermal and chemical stability in oxidizing and reducing atmospheres, and hence the complex oxide can be appropriately used as a constituent material of the manganese reaction layer that is suitable for the object of the invention.

Figure 2:
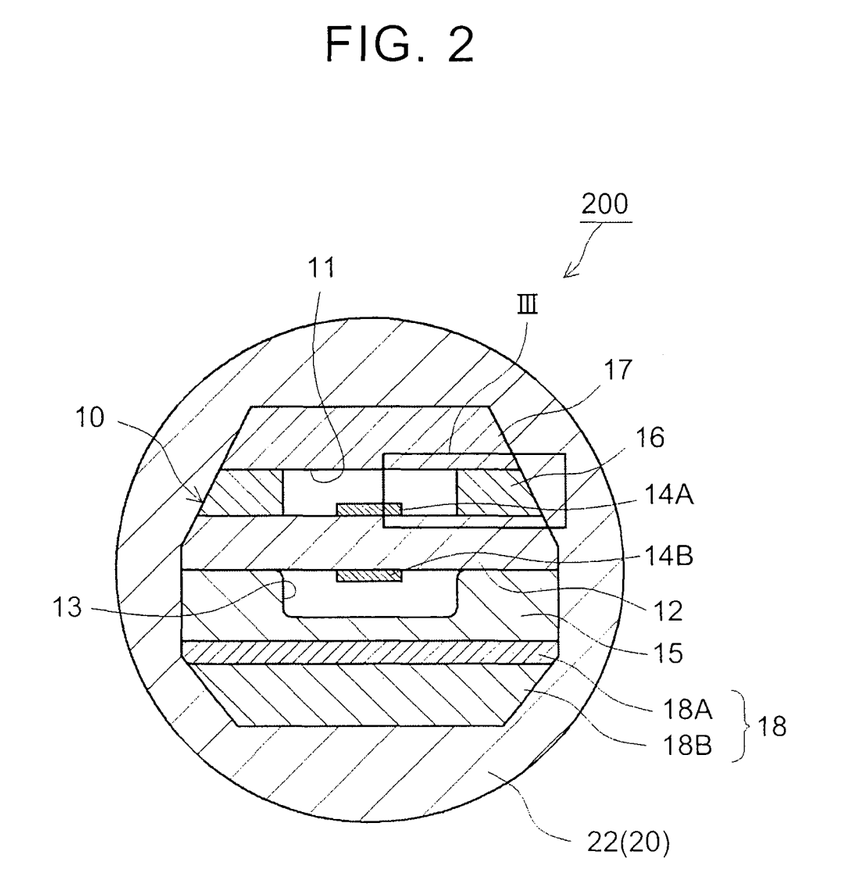
FIG. 2 is a cross-sectional diagram illustrating schematically an exhaust gas sensor according to a second embodiment of the invention.
Figure 3:
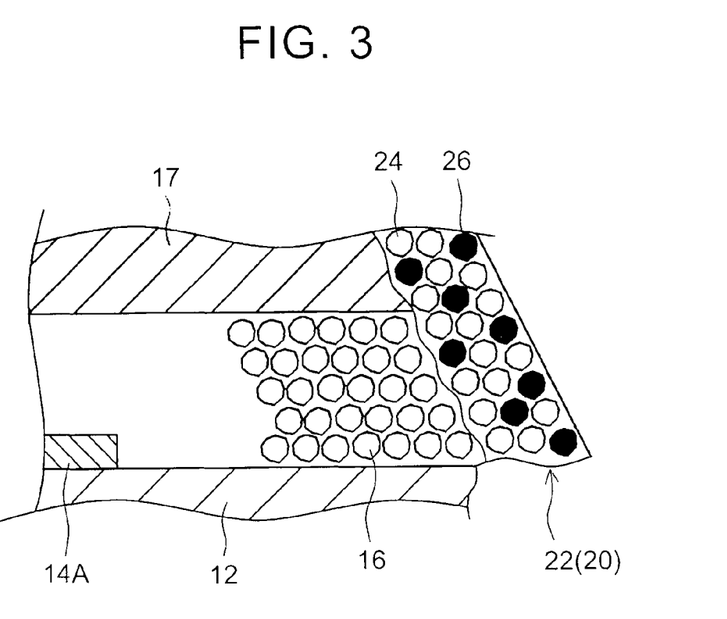
FIG. 3 is an enlarged-view diagram of an essential portion illustrating an enlargement of region III in FIG. 2.

An explanation follows next, with reference to FIG. 2 and FIG. 3, on an exhaust gas sensor 200 according to a second embodiment of the invention.

In the embodiment, a porous protective layer 22 is formed so as to cover the entire surface of the sensor element 10, as illustrated in FIG. 2. The porous protective layer 22 is made up of a porous body in which multiple ceramic particles are bonded to each other. The porous protective layer 22 is provided in order to suppress water breakage of the sensor element 10 by water that reaches the latter. The manganese reaction layer 20 is formed through addition, to the porous protective layer 22, of a substance that contains an element capable of generating a complex oxide having manganese (typically, a spinel-structure or perovskite-structure complex oxide having manganese).

FIG. 3 is a diagram illustrating an enlargement of region III in FIG. 2. As illustrated in FIG. 3, the porous protective layer 22 has ceramic particles 24. For instance, the ceramic particles 24 are made up of a ceramic such as a metal oxide having alumina, spinel, mullite or the like as a main constituent, or a metal carbide of silicon carbide or the like. The ceramic particles 24 may support precious metal particles, as the case may require. Precious metal particles that may be used include, for instance, palladium or rhodium, singly, or an alloy of two or more metals from among palladium, rhodium and platinum. The average particle size of the ceramic particles 24 is about 12 µm or less. For instance, there are preferably used ceramic particles having an average particle size of about 10 µm or less, more preferably 8 µm or less, and particularly preferably 6 µm or less. Water resistance is enhanced by virtue of the fact that the porous protective layer 22 is configured out of such small-diameter particles.

The porous protective layer 22 contains a substance (typically, in particulate form) 26 that contains an element capable of generating a complex oxide having manganese. As a result, the porous protective layer 22 serves also as the manganese reaction layer 20 according to the invention.

The porous protective layer 22 has one, two or more elements from among Zn, B, Ca, Ba, Sr, V and Y, as the element capable of generating a complex oxide having manganese. The substance 26 that has such elements may be amorphous glass, such as the above-described one, or a crystalline oxide. Preferably, the addition amount of the substance 26 having the abovementioned element in the porous protective layer 22 is 10 mass % or more (or 15 mass % or more), and further preferably 20 mass % or more, with respect to the total mass of the porous protective layer.

Reactions with a manganese oxide in the exhaust gas can proceed smoothly, and the manganese oxide can be replaced by a complex oxide (typically, a spinel-structure or perovskite-structure complex oxide) having manganese, by prescribing the content of the substance 26 that has the abovementioned element to lie within the above ranges. A configuration may also be adopted in which no ceramic particles 24 are used, and the porous protective layer 22 is made up substantially only of the substance (for instance, oxide) 26 that has the abovementioned element.

The porous protective layer 22 to which the substance that has the abovementioned element is added can be formed, for instance, in the manner described below. Firstly, a slurry is prepared in which the ceramic particles 24, the substance that has the abovementioned element (typically, in powder form) 26, and other components that form the porous protective layer (for instance, a binder, a dispersant) are dissolved in an appropriate solvent (for instance, water). The slurry is applied onto the surface of the sensor element 10, followed by drying; as a result there can be obtained the porous protective layer 22 having added thereto the substance 26 that has the abovementioned element.

In the above embodiment, the sensor element 10 is configured through layering of the solid electrolyte layer 12, the heater layer 18, and the porous diffusion resistance layer 16. The measurement electrode 14A and the reference electrode 14B are respectively provided on either side of the solid electrolyte layer 12. The heater layer 18 has the heating resistor 18A that generates heat when energized. Exhaust gas goes through the diffusion resistance layer 16 to be introduced into the measurement electrode 14A. The porous protective layer 22 is formed so as to cover at least the diffusion resistance layer 16. The manganese reaction layer 20 is formed through addition, to the porous protective layer 22, of a substance that contains an element capable of generating a complex oxide having manganese (typically, a spinel-structure or perovskite-structure complex oxide). In this case, the porous protective layer 22 serves as the manganese reaction layer 20, and hence the configuration of the exhaust gas sensor 200 can be simplified in that the manganese reaction layer 20 need not be provided separately. The manganese reaction layer 20 is disposed in the pathway of the exhaust gas, from the porous protective layer 22 up to the measurement electrode 14A via the diffusion resistance layer 16. As a result, it becomes possible to suppress yet more effectively delay in oxygen concentration changes in the exhaust gas that reaches the measurement electrode 14A.

Experimental examples relating to the invention are explained next, but the invention is not meant to be limited to the features described in the Experimental examples.

Figure 4:
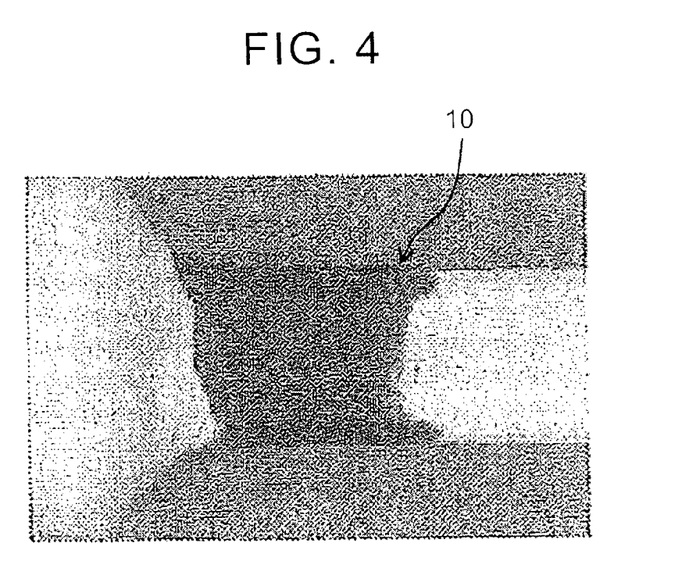
FIG. 4 is an image of a sensor element used in an example.

In Experimental example 1, a dense manganese reaction layer 20 made up of amorphous glass was formed on the surface of the sensor element 10. Specifically, raw material powders of the manganese reaction layer 20 were blended and mixed at predetermined ratios, as given in Tables 1 and 2. Thereafter, the resulting mixture was dispersed in water, to prepare a glaze slurry. The glaze slurry was applied onto the surface of the sensor element 10 (black portion in FIG. 4), followed by baking at 950° C. for 1 hour. An exhaust gas sensor 100 (example) was thus obtained in which the manganese reaction layer 20, made up of the amorphous glass, was formed on the surface of the sensor element 10.

TABLE 1

| Composition (mass %) | | | | | | | | | |
|---|---|---|---|---|---|---|---|---|---|
| ZnO | $B_2O_3$ | $SiO_2$ | $Al_2O_3$ | CaO | $K_2O$ | $Li_2O$ | NiO | CoO | $MoO_2$ |
| 19.30 | 27.00 | 33.50 | 3.71 | 0.16 | 10.50 | 1.72 | 1.22 | 0.99 | 0.43 |

Total: 98.53 mass %

TABLE 2

| Minor component composition | | | | | | | | |
|---|---|---|---|---|---|---|---|---|
| MgO | BaO | $Na_2O$ | $La_2O_3$ | SrO | $ZrO_2$ | SnO | $Y_2O_3$ | $HfO_2$ |

Total: 1.47 mass %

Figure 5:
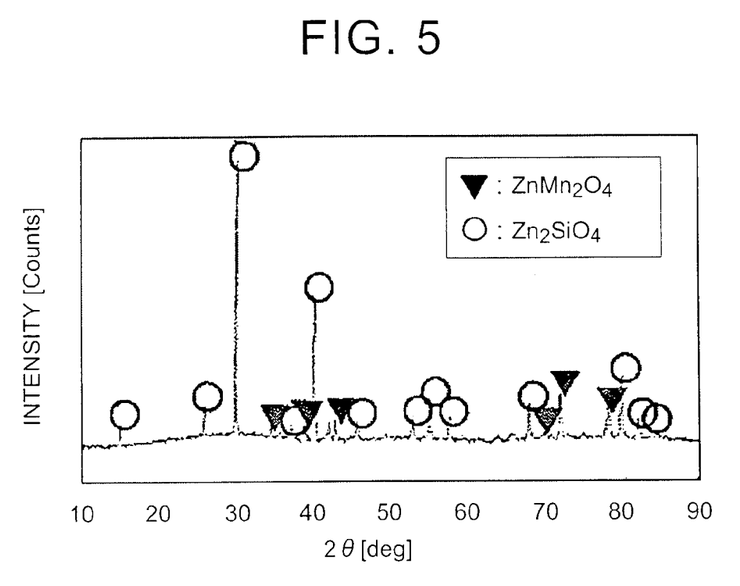
FIG. 5 is a diagram illustrating an X-ray diffraction pattern after a Mn endurance test of a manganese reaction layer according to an example.

The gas sensor 100 thus obtained was subjected to a Mn endurance test. The Mn endurance test was performed by applying $Mn_3O_4$ powder onto the manganese reaction layer 20, followed by firing at 700° C. for 24 hours. FIG. 5 illustrates an X-ray diffraction pattern after the Mn endurance test. FIG. 5 revealed that a spinel-structure complex oxide ($ZnMn_2O_4$) was generated through reaction between $Mn_3O_4$ and the Zn component in the manganese reaction layer.

A sensor output waveform of the gas sensor after the above-described Mn endurance test was measured. The sensor output waveform was measured by assembling the gas sensor of the example onto a gas detector, and holding the sensor in a test gas having a predetermined oxygen concentration. The sensor output waveform was measured before and after the above-described Mn endurance test. As a comparative example, a gas sensor was prepared in which the manganese reaction layer 20 was not formed. The Mn endurance test was carried out then by applying $Mn_3O_4$ powder onto the sensor element 10 of this gas sensor, followed by firing at 700° C. for 24 hours. The sensor response output waveform of the comparative example after the Mn endurance test was measured under the same conditions as in the example. The results are depicted in FIG. 6.

Figure 6:
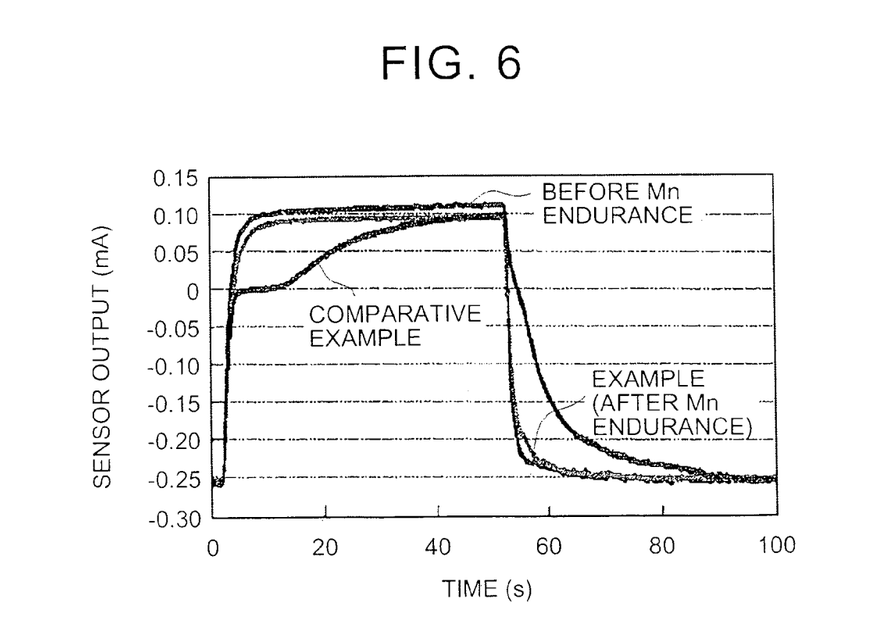
FIG. 6 is a diagram illustrating sensor output waveforms of exhaust gas sensors according to an example and a comparative example.

In the comparative example, where no manganese reaction layer 20 was formed on the surface of the sensor element 10, the oxygen concentration around the sensor element 10 varied on account of redox reactions of $Mn_3O_4$, and the sensor output response was significantly delayed as a result, as illustrated in FIG. 6. In the example, where the manganese reaction layer 20 was formed on the surface of the sensor element 10, by contrast, the sensor output waveform exhibited virtually no changes before and after Mn endurance, and good results were obtained. It is deemed that in the example, thus, $Mn_3O_4$ is replaced by a stable spinel-structure complex oxide ($ZnMn_2O_4$), and, as a result, changes in oxygen concentration in the exhaust gas around the sensor element 10 can be curtailed, and the sensor response delay can be reduced.

Figure 7:
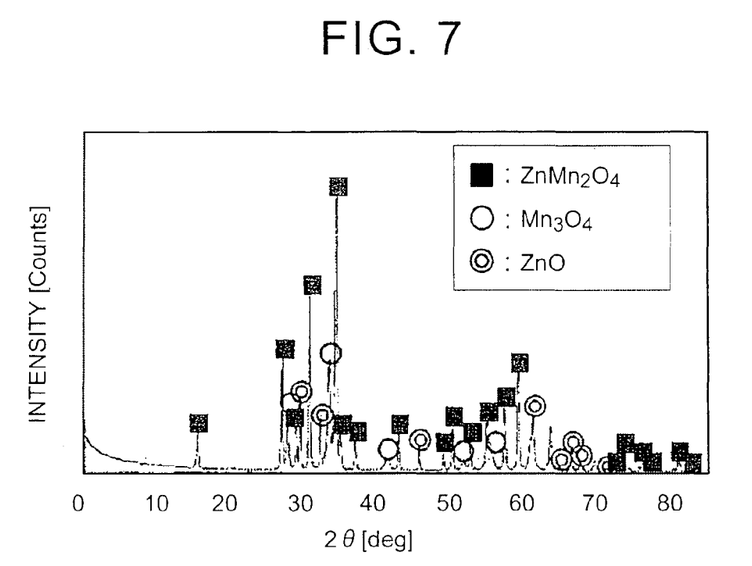
FIG. 7 is a diagram illustrating an X-ray diffraction pattern after firing of ZnO and $Mn_3O_4$.

The below-described test was performed, as Experimental example 2, in order to check the reactivity between ZnO and $Mn_3O_4$. Herein, ZnO powder and $Mn_3O_4$ powder were weighed to obtain a 1:1 mass ratio, and the mixture was compacted into pellets. The pellets were fired at 700° C. for 24 hours. The pellets after firing were crushed and the X-ray diffraction pattern thereof was measured. The results are depicted in FIG. 7. FIG. 7 revealed that a spinel-structure complex oxide ($ZnMn_2O_4$) was generated through reaction between ZnO and $Mn_3O_4$.

Figure 8:
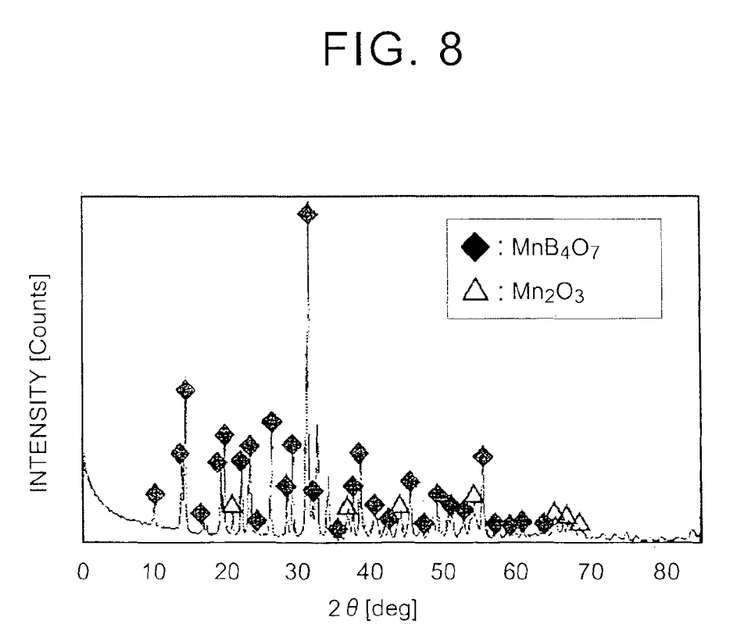
FIG. 8 is a diagram illustrating an X-ray diffraction pattern after firing of $B_2O_3$ and $Mn_3O_4$.

The reactivity between $B_2O_3$ and $Mn_3O_4$ was assessed in accordance with a procedure identical to the procedure for checking the reactivity between ZnO and $Mn_3O_4$ in Experimental example 2. The results are depicted in FIG. 8. FIG. 8 revealed that a complex oxide having manganese ($MnB_4O_7$) was generated through reaction between $B_2O_3$ and $Mn_3O_4$.

Figure 9:
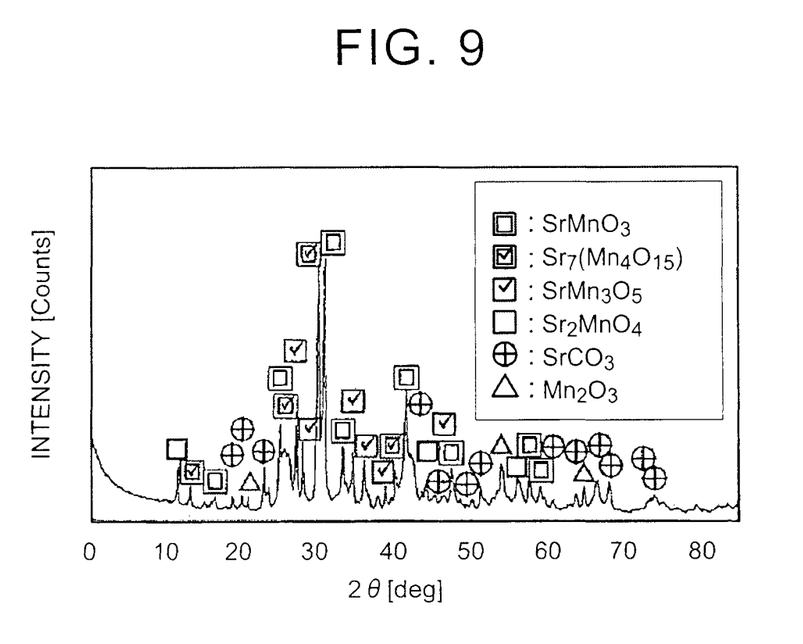
FIG. 9 is a diagram illustrating an X-ray diffraction pattern after firing of SrO and $Mn_3O_4$.

The reactivity between SrO and $Mn_3O_4$ was assessed in accordance with a procedure identical to the procedure for checking the reactivity between ZnO and $Mn_3O_4$ in Experimental example 2. The results are depicted in FIG. 9. FIG. 9 revealed that a perovskite-structure complex oxide ($SrMnO_3$) was generated through reaction between SrO and $Mn_3O_4$.

Figure 10:
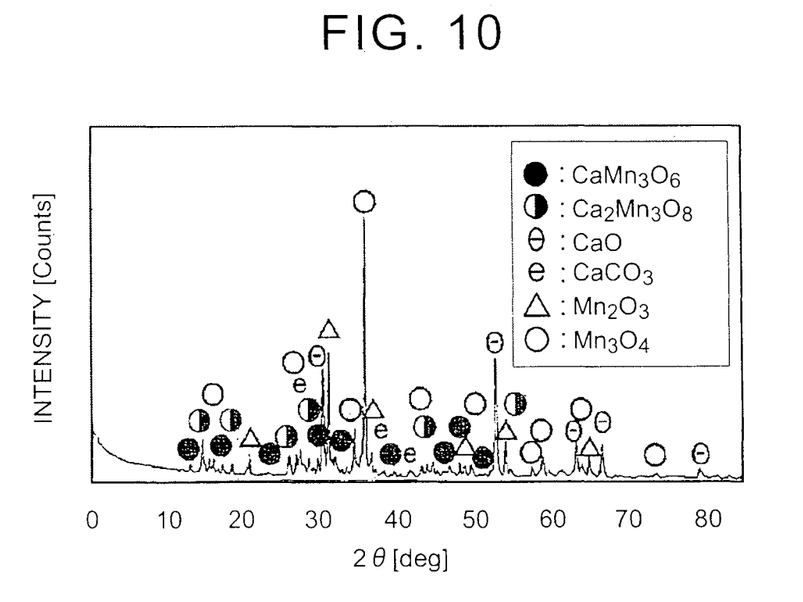
FIG. 10 is a diagram illustrating an X-ray diffraction pattern after firing of CaO and $Mn_3O_4$.

The reactivity between CaO and $Mn_3O_4$ was assessed in accordance with a procedure identical to the procedure for checking the reactivity between ZnO and $Mn_3O_4$ in Experimental example 2. The results are depicted in FIG. 10. FIG. 10 revealed that a complex oxide having manganese ($CaMn_3O_6$) was generated through reaction between CaO and $Mn_3O_4$.

Figure 11:
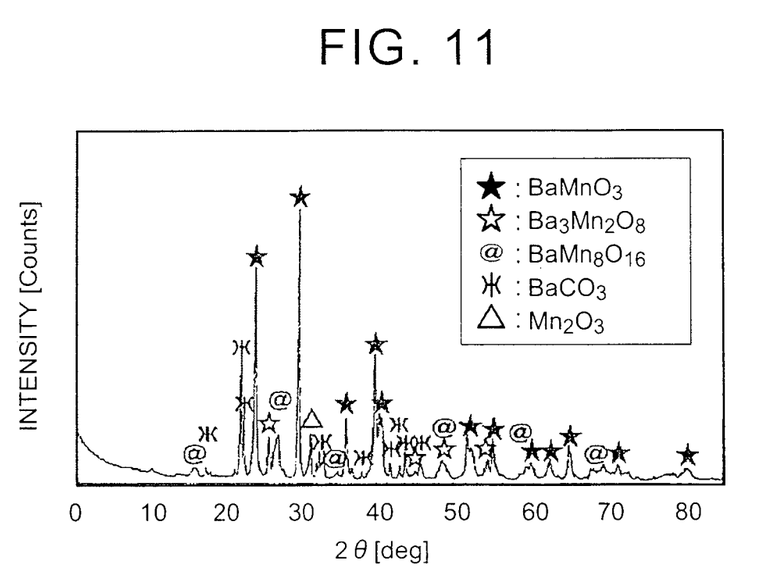
FIG. 11 is a diagram illustrating an X-ray diffraction pattern after firing of BaO and $Mn_3O_4$.

The reactivity between BaO and $Mn_3O_4$ was assessed in accordance with a procedure identical to the procedure for checking the reactivity between ZnO and $Mn_3O_4$ in Experimental example 2. The results are depicted in FIG. 11. FIG. 11 revealed that a perovskite-structure complex oxide ($BaMnO_3$) was generated through reaction between BaO and $Mn_3O_4$.

Figure 12:
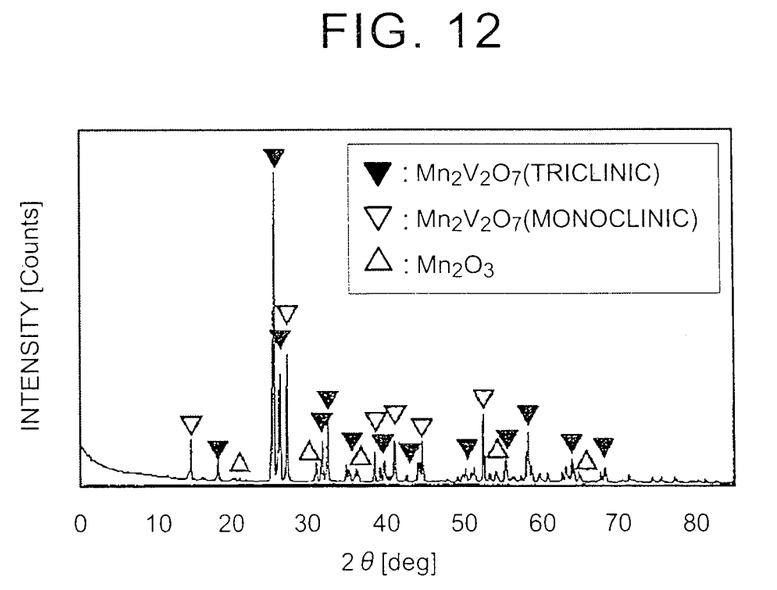
FIG. 12 is a diagram illustrating an X-ray diffraction pattern after firing of $V_2O_4$ and $Mn_3O_4$.

The reactivity between $V_2O_4$ and $Mn_3O_4$ was assessed in accordance with a procedure identical to the procedure for checking the reactivity between ZnO and $Mn_3O_4$ in Experimental example 2. The results are depicted in FIG. 12. FIG. 12 revealed that triclinic and monoclinic complex oxides having manganese ($Mn_2V_2O_7$) were generated through reaction between $V_2O_4$ and $Mn_3O_4$.

Figure 13:
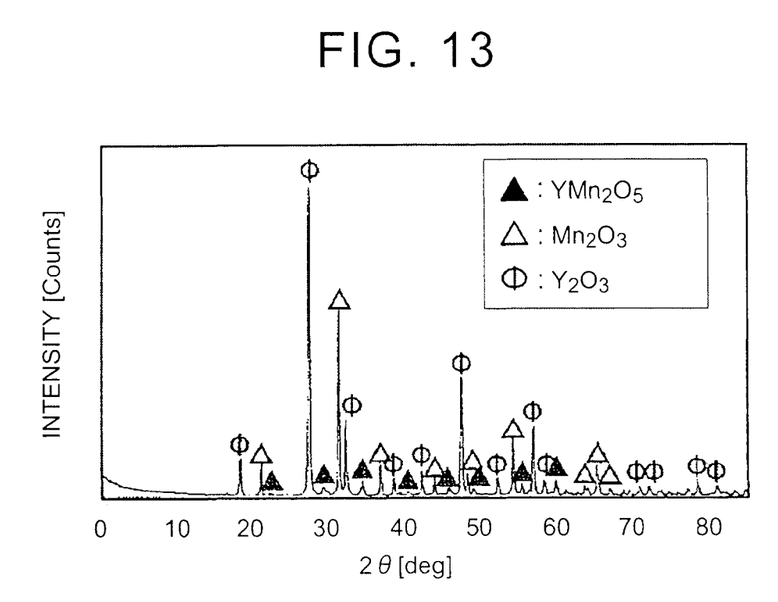
FIG. 13 is a diagram illustrating an X-ray diffraction pattern after firing of $Y_2O_3$ and $Mn_3O_4$.

The reaction between $Y_2O_3$ and $Mn_3O_4$ was assessed in accordance with a procedure identical to the procedure for checking the reactivity between ZnO and $Mn_3O_4$ in Experimental example 2. The results are depicted in FIG. 13. FIG. 13 revealed that a complex oxide having manganese ($YMn_2O_5$) was generated through reaction between $Y_2O_3$ and $Mn_3O_4$.

All the above suggested that an oxide that contains one, two or more elements from among Zn, B, Ca, Ba, Sr, V and Y can be used as the element capable of generating a complex oxide having manganese.

Figure 14:
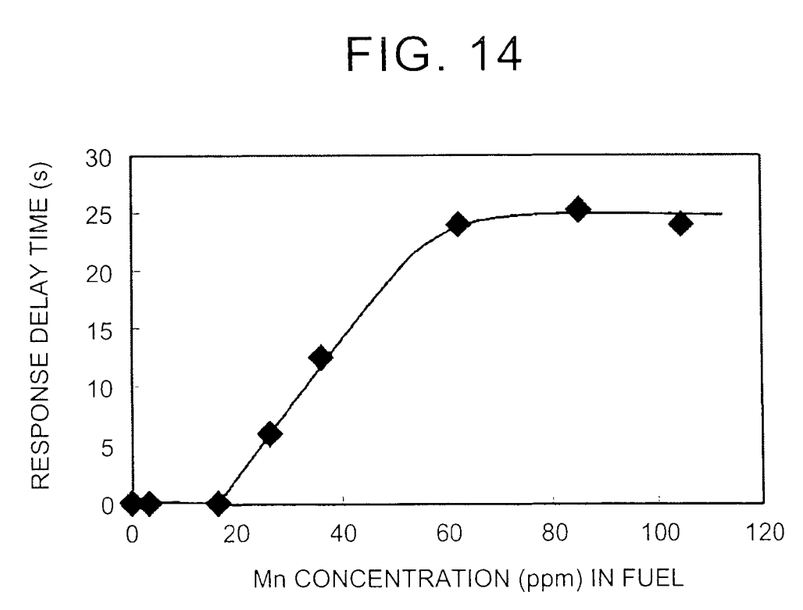
FIG. 14 is a graph illustrating a relationship between Mn concentration in fuel and response delay time.

In Experimental example 3, the below-described test was performed in order to verify the influence that Mn in fuel exerts in sensor response. In the test, a conventional gas sensor, having no manganese reaction layer formed on the surface of a sensor element, was disposed in the exhaust system of an engine. There was measured the sensor output after endurance involving travel for 150,000 miles (about 240,000 km) using a fuel to which methylcyclopentadienyl manganese tricarbonyl (MMT), as an octane booster, had been added in an arbitrary concentration. The sensor response delay time was assessed through comparison with the sensor output before endurance. The results are depicted in FIG. 14. FIG. 14 is a graph illustrating the relationship between Mn concentration (ppm) in fuel and response delay time (s).

As FIG. 14 shows, the response delay time tended to increase once the Mn concentration in fuel exceeded 20 ppm. In particular, the response delay time reached about 25 seconds as the Mn concentration in fuel exceeded 60 ppm. Exhaust gas sensors in which the technology disclosed herein is to be preferably used include, for instance, exhaust gas sensors for detecting the oxygen concentration or air-fuel ratio in the exhaust gas of an engine that utilizes fuel with high Mn concentration, with a content of Mn in excess of 20 ppm. Examples include, for instance, an exhaust gas sensor that is used in an engine that utilizes a fuel having a Mn concentration of 20 ppm or higher (for instance, 40 ppm or higher, typically 60 ppm or higher, or 100 ppm or higher, and particularly 200 ppm or higher). Manganese oxide adheres readily onto the sensor element of an exhaust gas sensor for detecting the oxygen concentration or air-fuel ratio in the exhaust gas of an engine that utilizes such fuels having a high Mn concentration, and sensor response delay arising from the manganese oxide is likely to occur. Therefore, the exhaust gas sensor of the embodiments of the invention, which allows effectively preventing sensor response delay caused by manganese oxide, can be suitably used, in particular, in engines that utilize fuels having a high Mn concentration, such as the abovementioned ones.

Embodiments of the invention have been explained in detail, but the embodiments are merely exemplary in character, and are not meant to limit the invention in any way. The invention encompasses also all manner of variations and modifications of the embodiments exemplified above.

The invention claimed is:

1. An exhaust gas sensor configured to detect an oxygen concentration or air-fuel ratio in exhaust gas, comprising:
    a sensor element that detects an oxygen concentration or air-fuel ratio; and
    a manganese reaction layer formed on at least part of a surface of the sensor element and formed of a substance containing an element capable of generating a complex oxide having manganese through reaction with a manganese oxide in the exhaust gas, wherein
    the exhaust gas sensor is configured to detect the oxygen concentration or air-fuel ratio in exhaust gas of an internal combustion engine that utilizes a fuel having a Mn concentration in excess of 20 ppm.

2. The exhaust gas sensor according to claim 1, wherein the manganese reaction layer contains at least one element from among Zn, B, Ca, Ba, Sr, V and Y, as the element capable of generating the complex oxide having manganese.

3. The exhaust gas sensor according to claim 2, wherein at least part of the manganese reaction layer contains amorphous glass;
    a glass matrix that makes up the amorphous glass includes Si, B, Al, R and M as main constituents, wherein R is at least one element from among Li, Na and K, and wherein M is at least one element from among Zn, Ca, Ba, Sr, V and Y;
    a mass ratios of main components, in terms of oxide, with an entirety of the glass matrix as 100 mass %, are
    $SiO_2$ 25 mass % to 40 mass %,
    $B_2O_3$ 20 mass % to 35 mass %,
    $Al_2O_3$ 1 mass % to 10 mass %,
    $R_2O$ 5 mass % to 20 mass %, and
    M oxide 0 mass % to 25 mass %; and
    a total of the main components is 80 mass % or more.

4. The exhaust gas sensor according to claim 3, wherein the glass matrix includes Si, B, Al, K and Zn as the main constituents;
    the mass ratios of the main components, in terms of oxide, with the entirety of the glass matrix as 100 mass %, are
    $SiO_2$ 25 mass % to 40 mass %,
    $B_2O_3$ 20 mass % to 35 mass %,
    $Al_2O_3$ 1 mass % to 10 mass %,
    $K_2O$ 5 mass % to 20 mass %, and
    ZnO 15 mass % to 25 mass %; and
    the total of the main components is 80 mass % or more.

5. The exhaust gas sensor according to claim 2, wherein the manganese reaction layer is formed of oxide particles supported on the surface of the sensor element, and
    the oxide particles contain at least one element from among Zn, B, Ca, Ba, Sr, V and Y, as the element capable of generating the complex oxide having manganese.

6. The exhaust gas sensor according to claim 1, wherein the sensor element includes a stack of a solid electrolyte layer, a heater layer and a porous diffusion resistance layer;
    a pair of electrodes is provided on either respective side of the solid electrolyte layer;
    the heater layer includes a heating element that generates heat through energization;
    the diffusion resistance layer is configured to let the exhaust gas through in such a manner that the exhaust gas is introduced to either of the pair of electrodes; and
    the manganese reaction layer is formed of a dense body that does not let the exhaust gas through, and is formed at a region that excludes the diffusion resistance layer.

7. The exhaust gas sensor according to claim 1, wherein the sensor element includes a stack of a solid electrolyte layer, a heater layer and a porous diffusion resistance layer;
    a pair of electrodes is provided on either respective side of the solid electrolyte layer;
    the heater layer includes a heating element that generates heat through energization;
    the diffusion resistance layer is configured to let the exhaust gas through in such a manner that the exhaust gas is introduced to either of the pair of electrodes;
    a porous protective layer covers the diffusion resistance layer; and
    the manganese reaction layer is formed by adding the substance containing the element capable of generating the complex oxide to the porous protective layer.

8. The exhaust gas sensor according to claim 7, wherein the porous protective layer covers an entire surface of the sensor element.

* * * * *